US008818822B2

(12) United States Patent
Ackerson et al.

(10) Patent No.: US 8,818,822 B2
(45) Date of Patent: Aug. 26, 2014

(54) HEALTH CARE ASSESSMENT AND ONLINE PROVIDER COMMUNICATION

(75) Inventors: Robert Scott Ackerson, Kansas City, MO (US); Brian Robert Carter, Kansas City, MO (US); Clay Patterson, Mission Hills, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 200 days.

(21) Appl. No.: 13/190,983

(22) Filed: Jul. 26, 2011

(65) Prior Publication Data

US 2013/0030834 A1 Jan. 31, 2013

(51) Int. Cl.
*G06Q 50/24* (2012.01)
*G06Q 50/00* (2012.01)
*G06Q 50/22* (2012.01)
*A61B 5/145* (2006.01)
*G06F 19/00* (2011.01)

(52) U.S. Cl.
CPC ............ *G06Q 50/24* (2013.01); *G06F 19/3431* (2013.01); *G06F 19/322* (2013.01); *G06F 19/363* (2013.01)
USPC ................................................. 705/3; 705/2

(58) Field of Classification Search
CPC ....... G06Q 50/00; G06Q 50/22; G06Q 50/24; G06Q 19/00
USPC .......................................................... 705/3
See application file for complete search history.

(56) References Cited

U.S. PATENT DOCUMENTS

| 2006/0064323 A1 | 3/2006 | Alleckson et al. |
| 2008/0215627 A1 | 9/2008 | Higgins et al. |
| 2009/0006133 A1* | 1/2009 | Weinert et al. ................. 705/3 |
| 2012/0232918 A1* | 9/2012 | Mack et al. .................... 705/2 |

FOREIGN PATENT DOCUMENTS

WO    WO 0028459    *    5/2000

OTHER PUBLICATIONS

Preinterview First Action Interview in U.S. Appl. No. 13/191,001 mailed Dec. 19, 2012, 4 pages.
Preinterview First Action Interview in U.S. Appl. No. 13/191,029 mailed Feb. 19, 2013, 4 pages.
Non-Final Office Action in U.S. Appl. No. 13/191,011 mailed Mar. 8, 2013, 12 pages.
First Action Interview Office Action in U.S. Appl. No. 13/191,001 mailed Mar. 14, 2013, 5 pages.
First Action Interview Office Action in U.S. Appl. No. 13/191,029 mailed Apr. 5, 2013, 10 pages.
Final Office Action in U.S. Appl. No. 13/191,001 mailed May 9, 2013, 11 pages.
Final Office Action in U.S. Appl. No. 13/191,029 mailed Jun. 6, 2013, 59 pp.
Final Office Action in U.S. Appl. No. 13/191,011 mailed Jul. 22, 2013, 22 pp.

* cited by examiner

*Primary Examiner* — Hiep V Nguyen
(74) *Attorney, Agent, or Firm* — Shook, Hardy & Bacon L.L.P.

(57) ABSTRACT

A graphical user interface provides clinical information in the form of a first health feed, patient-generated information in the form of a second health feed, and health care assessments in a third health feed. The graphical user interface may provide improved access to patient-generated information to the provider and improved access to clinical information to the patient or caretaker for the patient. Additional health feeds may include data from peripheral devices, third-party sponsored applications, or other forms of health feedback.

15 Claims, 8 Drawing Sheets

401

| JOHN DOE | GENDER: M | DOB: 1/5/75 | ID# 123456 |

- FEED 1 | FEED 2 ~403 | FEED 3 ~404 | FEED 4 ~405

VISIT SUMMARY

- CHIEF COMPLAINT:
- PHYSICIAN:
- TESTS PERFORMED:
- PHYSICAL ASSESSMENT:
- PATIENT PROVIDED INFORMATION:
- PATIENT ASSIGNMENT:
- PHYSICAL FOLLOW-UP:

| JOHN DOE | 411 | GENDER: M | DOB: 1/5/75 | ID# 123456 |

FEED 1 | FEED 2 | FEED 3 ~412 | FEED 4 ~413

PERSONAL HEALTH ASSESSMENT

Q1: WHAT IS YOUR PRIMARY RACE/ETHNICITY?
A1: ● X
   ○ Y
   ○ Z
   ○ W
Q2: DO YOU HAVE A PRIMARY CARE PROVIDER?
A2: ● Y
   ○ N
Q3: HOW OFTEN DO YOU EXERCISE?
A3: ● 5-7 X PER WEEK
   ○ 2-4 X PER WEEK
   ○ NEVER
   ○ OCCASIONALLY BUT NOT REGULARLY

}417

<<  <  PAGE 1 OF 5  >  >> ~418

HEALTH CARE ASSESSMENT AND ONLINE PROVIDER COMMUNICATION

CROSS-REFERENCE TO RELATED APPLICATIONS

This application is related to commonly assigned U.S. Patent Applications: U.S. patent application Ser. No. 13/191,029, filed Jul. 26, 2011, entitled "Online Patient and Health Care Provider Communication", U.S. patent application Ser. No. 13/191,001, filed Jul. 26, 2011, entitled "Health Care Biometric Surveillance and Online Provider Communication", and U.S. patent application Ser. No. 13/191,011, filed Jul. 26, 2011, entitled "Third-Party Site Connections for Online Health Care Communication", which are all filed concurrently herewith on the same date.

FIELD

The present disclosure relates to patient and provider communication interfaces.

BACKGROUND

Communication between patients and their providers is often limited to in-person or telephone interactions. Patients may keep records of their own health observations but lack the means to share this information with providers. Providers keep records of patient information that are not available to patients. However, it may be helpful for patients to have access to provider information. Access to both types of information may lead to insights into a patient's behaviors and health.

SUMMARY

Examples are directed graphical user interfaces that may be stored on one or more computer-storage media and executable by a computing device. The graphical user interface provides a clinical feed with provider content and a patient feed with patient content so that either/both the provider and the patient may access each other's contributions to the health care record. Additional feeds that may be displayed include an information feed from a peripheral device or a third-party feed. The additional feeds may further incorporate information provided by the patient and/or clinical feed.

In one example, a graphical user interface, which may be stored on one or more computer-storage media and executable by a computing device, comprises a first health feed display comprising clinical information for at least one patient, a second health feed display comprising patient-generated information for the at least one patient, and a third health feed display comprising one or more feedback displays providing patient feedback on the clinical information and the patient input information. The one or more feedback displays may further comprise clinical feedback on the patient-generated information of the second health feed display. The one or more feedback displays may comprise one or more patient questionnaires. The one or more feedback displays may comprise a summary of patient questionnaire results. The one or more feedback displays may comprise request displays for requests for patient activity, requests for clinic activity, or a combination thereof.

In another example, a graphical user interface, which may be stored on one or more computer-storage media and executable by a computing device, comprises a first health feed display comprising clinical information for at least one patient, a second health feed display comprising patient-generated information for the at least one patient, and a third health feed display comprising one or more feedback displays providing clinical feedback on the patient-generated information of the second health feed display. The one or more feedback displays may comprise patient feedback on at least one of the clinical feedback and the clinical information of the first health feed display. The one or more feedback displays may further comprise one or more patient questionnaires. The one or more feedback displays may further comprise a summary of patient questionnaire results. The one or more feedback displays may further comprise request displays for requests for patient activity, requests for clinic activity, or a combination thereof.

In another example, a method for providing health care assessments may comprise receiving provider input regarding a patient and storing provider input for the patient in a patient record. The method may further comprise determining based on patient rules provider information to display to a patient. The method may also comprise determining at least one patient input field to display for a patient and displaying the at least one patient input field for the patient to input information. The method may comprise receiving patient inputs and storing patient inputs in the patient record. The method may comprise determining at least one assessment for the patient based on patient inputs, the patient record, and patient rules and displaying the at least one assessment.

In addition, the at least one patient input field may comprise a patient questionnaire. The at least one assessment for the patient may comprise a questionnaire results summary. The at least one patient input field may be determined by patient type. The provider input may comprise medical test results from clinical testing.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 4A-C are illustrations of a graphical user interface with a plurality of health feeds.

Figure 7A:
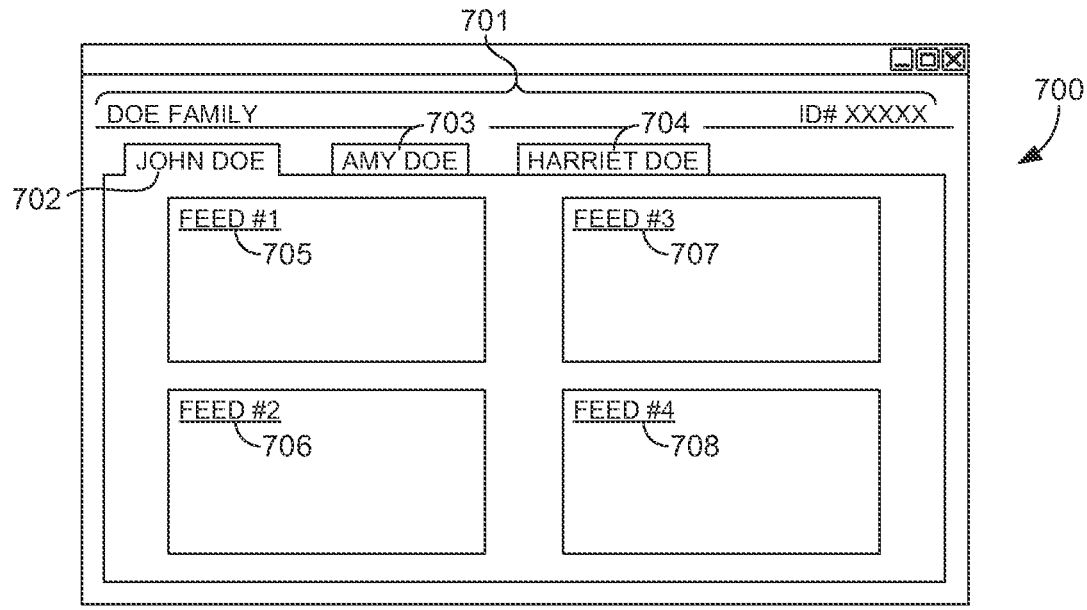
Figure 7B:
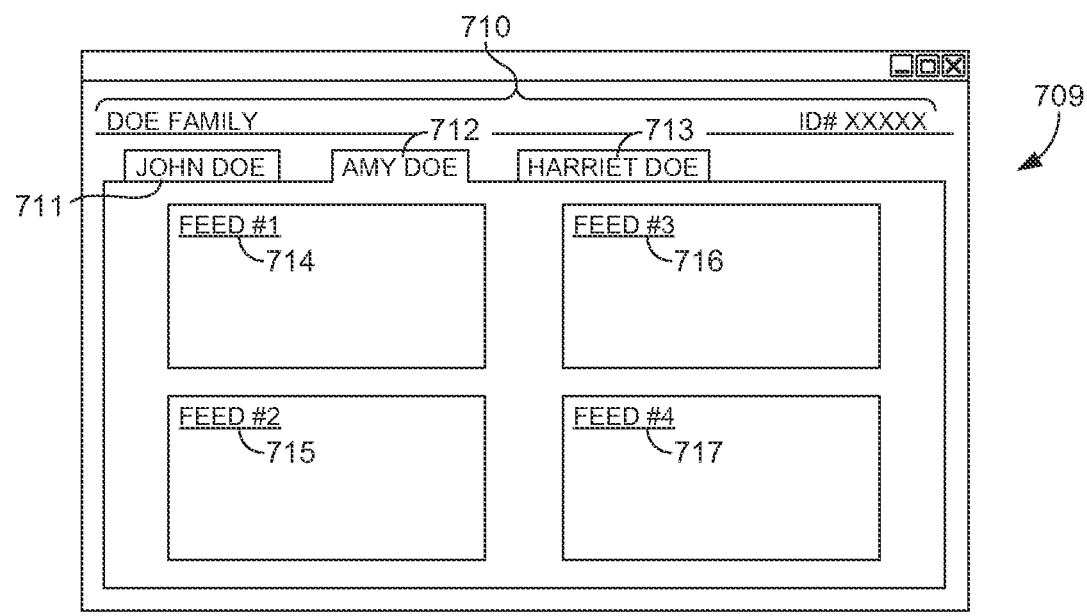
Figure 7C:
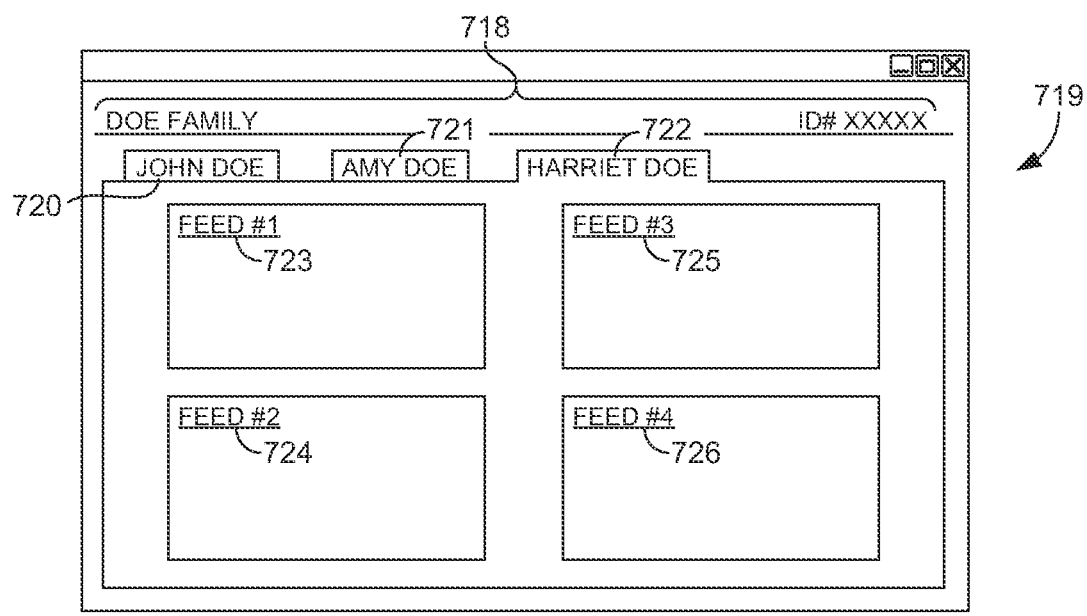

FIGS. 7A-C are illustrations of a graphical user interface with a plurality of patients.

Corresponding reference numerals indicate corresponding parts throughout the several views of the drawings.

DETAILED DESCRIPTION

Figure 1:
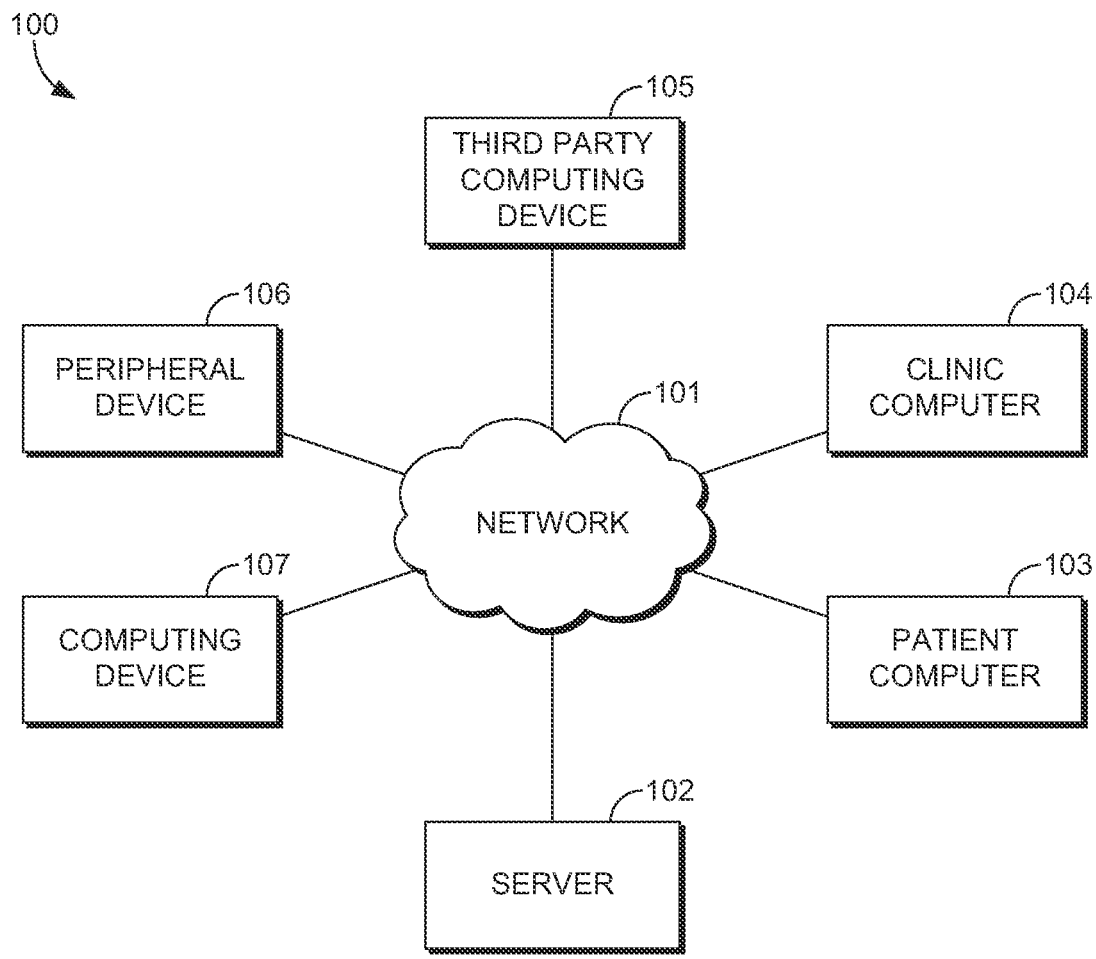
FIG. 1 is a schematic of a computing system for implementation of a graphical user interface.

FIG. 1 illustrates an exemplary computing environment 100 with which embodiments of the present invention may be implemented. Computing environment 100 is merely an example of one computing environment and is not intended to suggest any limitation as to the scope of use or functionality of the invention. Neither should the computing environment 100 be interpreted as having any dependency or requirement relating to any single component or combination of components illustrated therein.

The graphical user interface may be operational with numerous other general purpose or special purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The graphical user interface may be stored on one or more computers-storage media in the form of computer-executable instructions, such as program modules, that may be executed by one or more computers. Exemplary program modules comprise routines, programs, objects, components, and data structures that perform particular tasks or implement particular abstract data types. An exemplary graphical user interface may be practiced in distributed computing environments where tasks are performed by remote processing devices that are linked through a communications network. In a distributed computing environment, program modules may be located in association with local and/or remote computer storage media such as memory storage devices.

Returning to FIG. 1, the computing environment 100 comprises a general purpose computing device in the form of a control server 102. Exemplary components of the control server 102 may comprise a processing unit, internal system memory, and a suitable system bus for coupling various system components, including one or more databases, with the control server 102. The system bus may be any of several types of bus structures, including a memory bus or memory controller, a peripheral bus, and a local bus, using any of a variety of bus architectures. Exemplary architectures may comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102, the patient computer 103, the clinic computer 104, the third-party computing device 105, the peripheral device 106, and/or the computing device 107 typically includes therein, or has access to, a variety of computer-readable and computer-storage media, such as a database. Computer-storage media may be any available media that is accessible by the control server 102, the patient computer 103, the clinic computer 104, the third-party computing device 105, the peripheral device 106, and/or the computing device 107 and may be removable and/or non-removable media. Computer-storage media may be implemented in any method or technology for information storage, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102, the patient computer 103, the clinic computer 104, the third-party computing device 105, the peripheral device 106, and/or the computing device 107. Combinations of any of the above also may be included within the scope of computer-readable media. The computer storage media, such as a database, provides storage of computer-executable instructions, data structures, program modules, and other data for the control server 102, the patient computer 103, the clinic computer 104, the third-party computing device 105, the peripheral device 106, and/or the computing device 107.

The control server 102 may operate in a computer network 101 using logical connection to one or more remote computers. Remote computers illustrated in FIG. 1 include the patient computer 103, the clinic computer 104, the third-party computing device 105, the peripheral device 106, and/or the computing device 107. Patient computers 103 may be located at a patient's residence, in a location accessible to the patient, or portable. Clinic computers 104 may be located at a variety of locations in medical or research environments. Third-party computing devices may be associated with locations of third-party providers of various health related computing applications. The illustrated computers and computing devices may be personal computers, servers, routers, network PCs, peer devices, other common network nodes, personal digital assistants, smartphones, netbooks, tablet computers, or the like and may comprise some or all of the elements described above in relation to the control server 102. Peripheral devices 106 may be devices with network, Bluetooth, or other connectivity and may be scales, heart rate monitors, body mass composition monitors, pulse-oxygenation monitors, or any other device intended to measure a person's physiological parameters. Peripheral devices 106 may monitor a patient locally or remotely.

Exemplary computer networks 101 comprise local area networks (LANs) and/or wide area networks (WANs). Such networking environments are commonplace in offices, enterprise-wide computer networks, intranets, and the Internet. When utilized in a WAN networking environment, the control sever 102 might comprise a modem or other means for establishing communications over the WAN, such as the Internet. In a networked environment, program modules or portions thereof may be stored in association with the control server 102, a database associated with the control server, or any of the computers/computing devices 103-107. In one example, various application programs may reside on memory associated with any of the computers/computing devices 103-107. The network connections shown are merely exemplary and other means of establishing communications linkages between the computers, computing devices, and control server 102 may be utilized.

A user, such as a patient, a provider, or a third-party operator, may enter commands and information into the control server 102 or convey the commands and information to the control server 102 via one or more of the computers or computing devices illustrated in FIG. 1. Input may be provided through input devices, such as a keyboard, a mouse, trackball, touch pad, touch screen, or the like. Other input devices may include microphones, scanners, etc. Commands and information may be sent directly from a computing device 103-107 to the control server 102. In addition to a display, the control server 102 and/or computing devices 103-107 may comprise other peripheral output devices, such as speakers and a printer.

Although many internal components of the control server 102, the patient computer 103, the clinic computer 104, the third-party computing device 105, the peripheral device 106, and the computing device 107 are not shown, their components and interconnection are known. Accordingly, additional details concerning the internal construction of these devices are not further disclosed herein.

Figure 2:
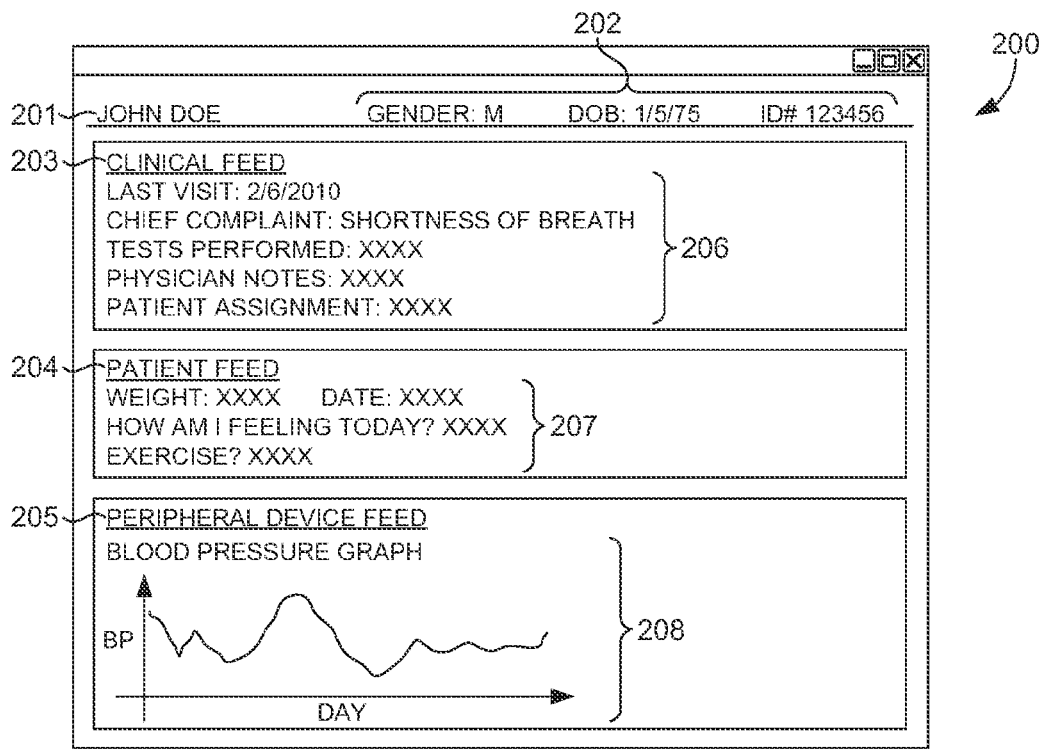
FIG. 2 is an illustration of a graphical user interface incorporating a first health feed and a second health feed.

Referring to FIG. 2, an illustration of an example of a graphical user interface comprising a first health feed display 203 and a second health feed display 204. The graphical user interface may include a display of the patient's name or other identifier 201, as well as other general patient information 202. The first health feed display 203 includes clinical information for at least one patient. In one example, the first health feed display 203 may include clinical information for more than one patient, such as for several members of a family or for members participating in a clinical study or other collaborative health event. Information 206 included in the first health feed display 203 may include a list of tests performed, treatments administered, physician notes or recommendations, and any other information of clinical relevance. Information 206 included in the first health feed display may be input by the provider via a clinic computer such as the computer 104 in FIG. 1 or via peripheral device 106 or via another computer device 107.

In FIG. 2, the second health feed display 204 includes patient-generated information 207 for the at least one patient. In another example, the second health feed display 204 may include patient-generated information for more than one patient, such as for several members of a family or for members participating in a clinical study or other collaborative health event. Information 207 generated and included in the second health feed 204 may include periodic weigh-ins, blood sugar monitoring, personal physical assessments, food diary entries, and any other health-related information that a patient may provide. Information 207 provided in the second health feed 204 may often be useful to the provider or clinic but difficult to obtain on a regular basis. Information 207 included in the second health feed display may be input by the patient or other user via a computer such as the patient computer 103 in FIG. 1 or via peripheral device 106 or via another computer device 107.

Referring to FIG. 2, in addition to the first health feed display 203 comprising clinical information and the second health feed display 204 comprising patient-generated information, the graphical user interface may further comprise a third health feed display 205 comprising a peripheral device feed. A peripheral device 106, as shown in FIG. 1, may be connected to the network or may be connected to a computing device 107, which is connected to the network. In another example, a peripheral device may be connected to the patient computer or the clinic computer or the third-party computer. A peripheral device may provide remote or local monitoring of the patient's physiological state. Referring back to FIG. 2, for example, a pulse-oxygenation monitor may provide regular updates that are displayed in the third health feed display 205. A blood pressure monitor may provide regular updates that are displayed in the third health feed display 205. A scale may provide patient weight updates that are tracked and displayed in the third health feed display 205. In another example, the peripheral device may be non-networked, such as a conventional scale, conventional blood glucose monitor, etc. In this case, a patient or person monitoring the patient may provide peripheral device feed data through a computing device. For example, each morning a mother tests the blood sugar of her child and inputs that information into a peripheral device interface on a computing device, which provides information to the peripheral device feed. Information included in the third health feed display may be input by the provider, the patient, or another user via a computer such as in FIG. 1 or via peripheral device 106 or via another computer device 107.

In one example, the graphical user interface may further comprise one or more feedback displays. The one or more feedback displays may provide feedback from the patient regarding the patient such as notes or other information to supplement the second health feed display. The one or more feedback displays may provide feedback from the patient regarding the clinic or clinician such as questions the patient has for the clinic or provider or suggestions for the clinic or provider. The one or more feedback displays may provide feedback from then clinic or provider for the patient such as recommendations or tasks to perform or the like. The one or more feedback displays may include requests from the patient or the clinician for the other party.

In another example, the graphical user interface may comprise feedback display 302 that may include a questionnaire 303 to provide additional patient status assessment. The questionnaire 303 may comprise a number of questions and answers, either multiple-choice or free-form, that a patient provides. The feedback display may include a questionnaire 303 formulated by the provider or may be a standardized form. Additionally, the feedback display may provide a summary of the questionnaire results and/or a health assessment or recommendations based on the answers to the questionnaire. For example, if a patient reports that he or she is feeling poorly despite adequate rest, the feedback display may recommend that the provider contact the patient or the patient contact the provider. The feedback display with results summary may make additional recommendations to the patient with provider guidance. A questionnaire may also be provided for feedback of the patient's experience with the clinic or provider. Additionally or alternately, questionnaire may be provided to the clinic or clinician for a standardized assessment of the patient or other purposes.

Figure 3:
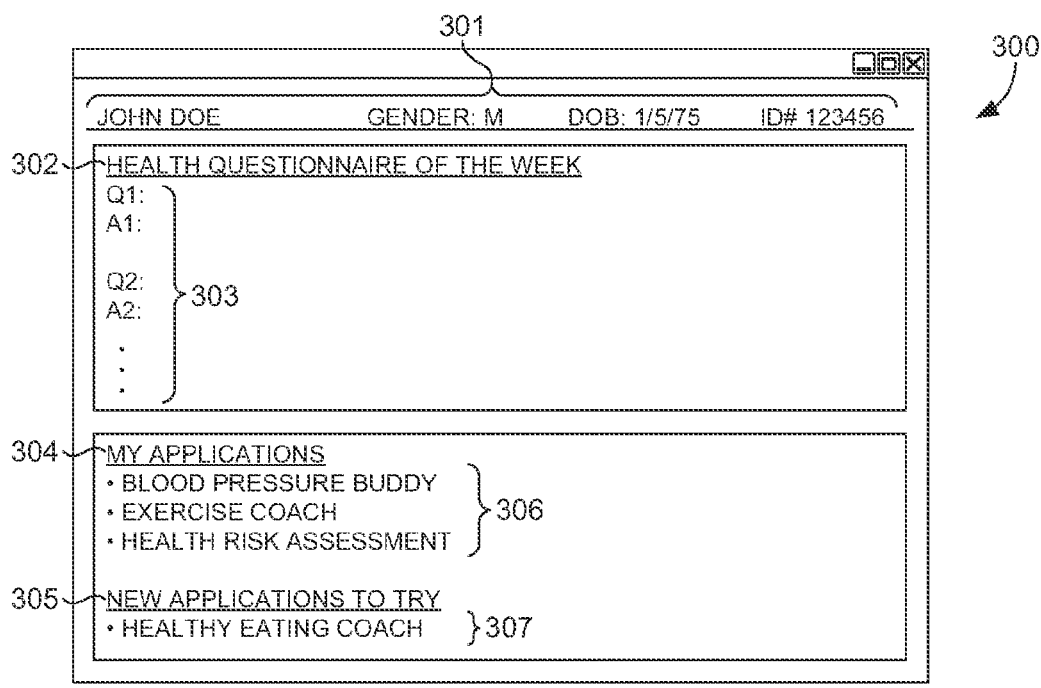
FIG. 3 is an illustration of a graphical user interface with additional health feed options

The graphical user interface may comprise displays for third-party applications 304 and displays for enrollment in third-party applications 305. Third-party applications may be administered via a third-party computing device such as illustrated in FIG. 1 item 105. Returning to FIG. 3, the third-party applications 306 may utilize data from the first health feed, the second health feed, or both. For example, if the second health feed display includes daily monitoring of blood pressure, a third-party application may be authorized by either the patient or the provider to correlate fluctuations in blood pressure to patient behavior or diet or other factors. A user may be a participant in a number of third-party applications 306, in which case, displays from the plurality of third-party applications may be displayed alone and toggled between or they may be displayed simultaneously. A third-party nutritional counseling application may use diet and exercise information provided by the patient in the second health feed display. The displays may also include options to enroll in additional applications 307. Third-party providers accessing the network as shown in FIG. 1 may gain aspects to all or a portion of the clinical information in the first health feed display and/or the patient-generated information in the second health feed display. Access may be assigned or otherwise granted by the patient or a person managing the patient, such as for a parent and child.

The first health feed and second health feed and, if provided, additional health feeds may be displayed as separate windows or tabs or sections within the interface. The plurality of feeds may be displayed together in a single feed of events or updates, which may be organized by input or entry date or ranked by priority. Additionally, the display may be configured for display to a provider, to a patient, or to a third-party. For example, a provider graphical user interface may be configured to highlight or emphasize some aspects of patient information, such as blood pressure or blood sugar level, that a provider may find most useful in assessing the patient's condition and/or providing feedback. A patient-oriented graphical user interface may be configured to highlight a provider's suggestions or other aspects of the provider's input. The graphical user interface may include a display options portion that allows whoever is using the interface to select various aspects of each feed to highlight or minimize.

In one example, the graphical user interface may be configured to display health feeds for members of a family and managed by one or more than one member. For example, a parent may be provided with additional feeds for each child and have convenient access to provider information. In another example, the graphical user interface may be configured to display health feeds for members of a clinical study in a collaborative environment or may be managed by the administrator of the clinical study.

Referring to FIGS. 4A-B, an additional example of a graphical user interface is provided. The exemplary graphical user interface allows a user to tab between various feeds 402-405, which varies the highlighted feed in the user interface 400, 408, 419. In FIG. 4A, a graphical user interface 400 may include a patient identification display 401. The patient identification 400 may change as a user selects between patients in a multi-patient interface. For example, a user may be viewing feeds for members of his or her family, in which case, the patient identification 400 will change depending on the member that is displayed. A series of tabs 402-405 or other graphical form of content separation may be provided. For example, the first health feed 402 may be selected and may display clinical information for the patient indicated in the identification 401. The first health feed content 407 may include clinical information such as tests performed and physician notes. The first health feed content may be edited to include whatever information the provider wishes the user to have access to. The first health feed 402 may also include a scroll bar or page turning option to display extended patient history.

Referring to FIG. 4B, an example of a graphical user interface may include a second health feed 411 that may be selected between tabs 410-413 or another means for separating or organizing content. For example, content illustrated in tabs 410-413 may be selected by icons or windows, which expand to show the health feed content. The second health feed 411 may include patient-generated information 417. The information may be input by any means, for example, a questionnaire may be provided to a patient. In another example, a patient may keep a journal or notes of his or her physical and mental state. A patient may self-monitor his or her physical parameters and supply them to the second health feed 411. In the questionnaire example, a patient may complete a periodic personal health assessment 414. Questions 415 asked in the assessment may be standardized or selected by the provider. Answers 416 to the questions may be multiple choices or other standardized testing forms or may include a free form answer box. In addition to the questionnaire, the content of the second health feed 411 may be extensive and the graphical user interface may include a scroll bar or page navigation 418.

Figure 4C:
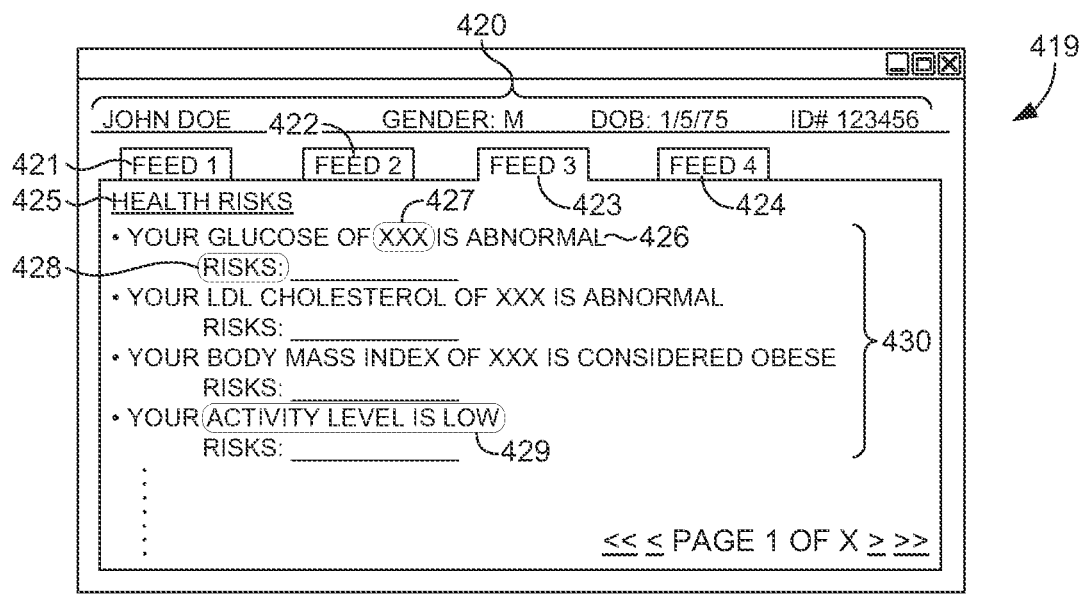

Referring to FIG. 4C, an example of a third-party application that utilized information from the clinical information in the first health feed display 421 and patient-generated information of the second health feed 422 is illustrated in the third application display 423. The third-party application may be authorized to access the information of the other feeds by the patient, provider, or other user. The third-party application may utilize this information to provide additional suggestions or information to the user 430. The user may be a parent supervising the health of a dependent, who is the patient 420 displayed in the interface. In one example, the third-party application may retrieve data 427 from the clinical information, may determine that the patient is at risk 426, and assess various risk factors 428. In another example, the third-party application may retrieve data from the patient generated information or a peripheral device feed and provide additional assessments 429. The third-party application may combine the input from the various feeds to provide a third application display 423. The third application display may also display suggested additional third-party applications for the patient or user to enroll in, such as a weight loss or exercise motivation application.

Additional feeds, such as feedback feed displays, peripheral device feed displays, and electronic visit displays may be provided via additional tabs 424, windows, icons, etc. In one example, an electronic visit display may include an internet-based consultation between the patient and provider. The electronic visit display may include other forms of interaction between the patient and provider that are recorded and arranged for display. The third application display 423 may be generated by processing information generated for the additional feeds as well as either the clinical information, the patient-generated information, or both. Additional application displays may be generated by authorizing a third-party application to process information generated for the additional feeds alone. The third-party application may process information from a peripheral display, such as a connected scale, and provide a weight-loss application.

Figure 5:
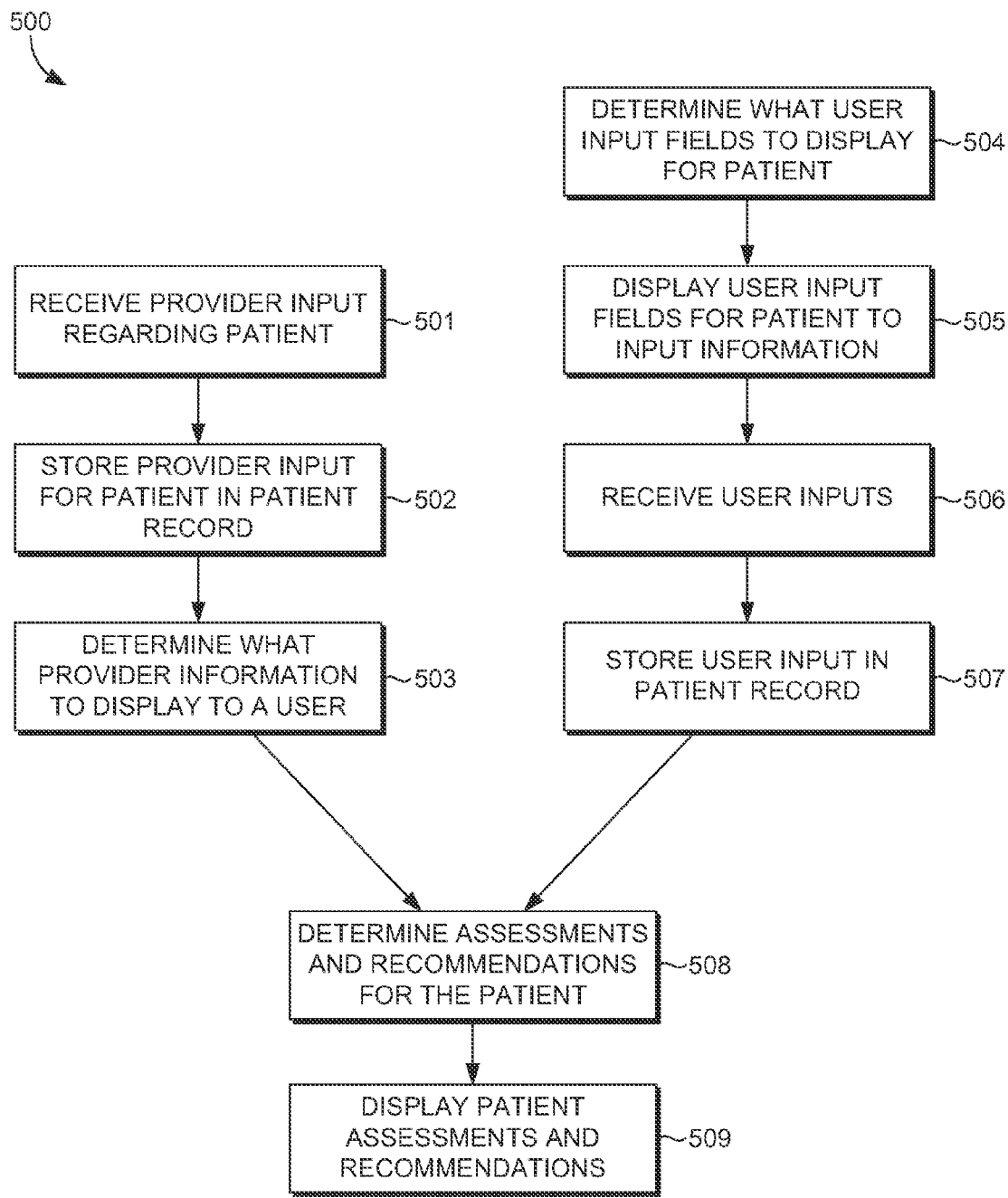
FIG. 5 is a schematic for a method for health care assessment and provider communication.

Referring to FIG. 5, an example of a method for health care assessment employing a graphical user interface as described above is illustrated. In step 501, provider input regarding a patient is received. The provider input for the patient may be stored in the patient record at step 502. The provider input to be displayed to a user may be determined at step 503. The information to be displayed to the user may be determined by using rules and information from the patient record. Information displayed may include lab results, visit summary, etc. In step 504, input fields to be displayed for the patient may be determined. The information to be displayed to the user may be determined using rules and information from the patient record. Information to be displayed may be determined by a number of factors, which may include smoking habits, weight, risk factors for diabetes, risk factors for cardiac events, pregnancy status, transplant status, etc. In step 505, the user input fields for the patient may be displayed to input patient information. In step 506, the user input may be received and then stored in the patient record in step 507. In step 508, assessments and recommendations for the patient may be determined based upon user inputs, patient record, and rules. Assessments and recommendations may include recommended programs, levels, risks, etc. In step 509, the patient assessments and recommendations may be displayed.

Figure 6:
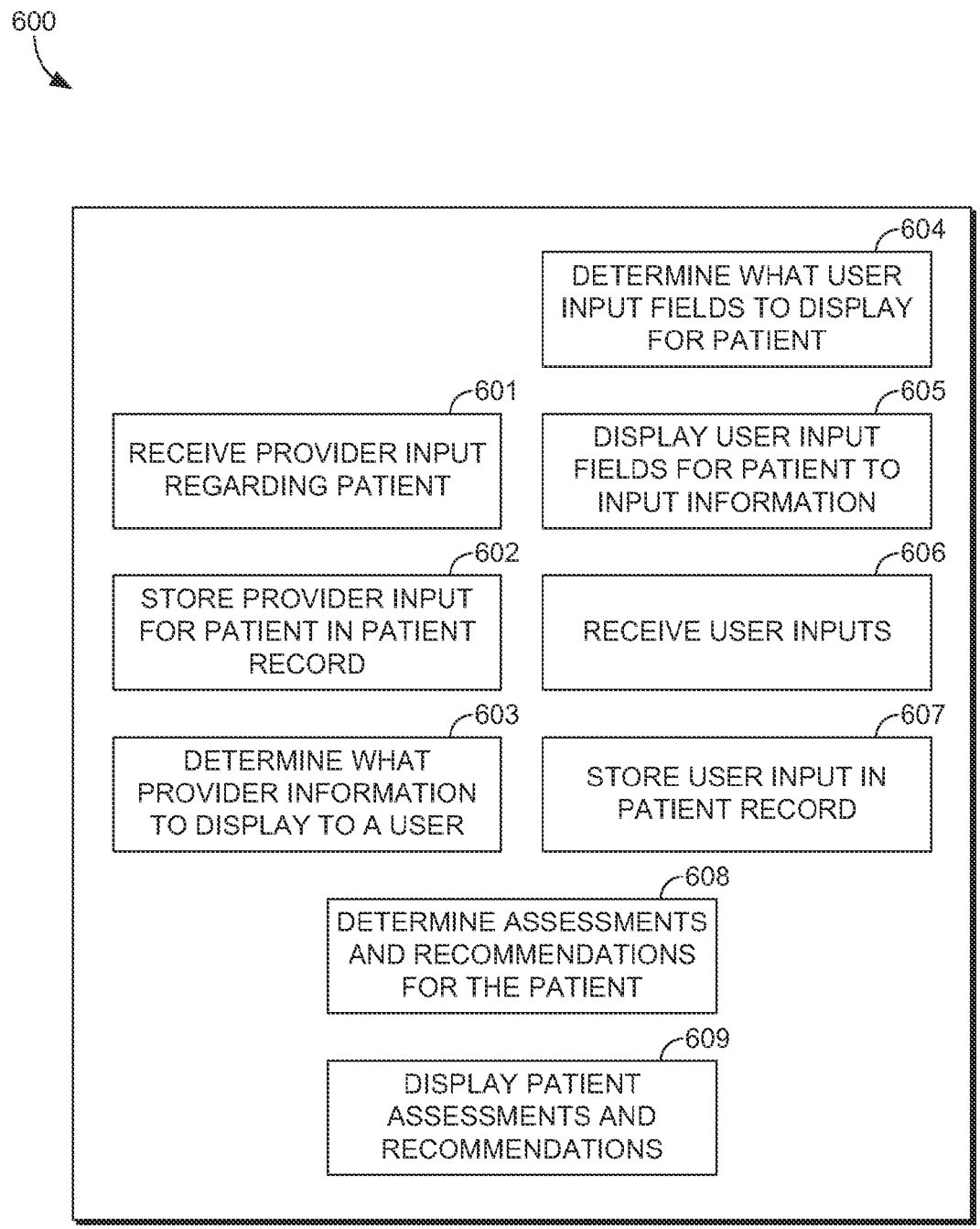
FIG. 6 is a schematic of a system of for health care assessment and provider communication.

Referring to FIG. 6, an example of a system for health care assessment employing a graphical user interface as described above is illustrated. In component 601, provider input regarding a patient is received. The provider input for the patient may be stored in the patient record at component 602. The provider input to be displayed to a user may be determined at item 603. The information to be displayed to the user may be determined by using rules and information from the patient record. Information displayed may include lab results, visit summary, etc. At component 604, input fields to be displayed for the patient may be determined. The information to be displayed to the user may be determined using rules and information from the patient record. Information to be displayed may be determined by a number of factors, which may include smoking habits, weight, risk factors for diabetes, risk factors for cardiac events, pregnancy status, transplant status, etc. At component 605, the user input fields for the patient may be displayed to input patient information. In item 606, the user input may be received and then stored in the patient record at 607. At item 608, assessments and recommendations for the patient may be determined based upon user inputs, patient record, and rules. Assessments and recommendations may include recommended programs, levels, risks, etc. At component 609, the patient assessments and recommendations may be displayed.

In FIGS. 7A-7B, an example of a graphical user interface for a user group is illustrated. In this example, the "Doe Family" includes three members, John Doe, Amy Doe, and Harriet Doe. Amy Doe may be John Doe's daughter, and Harriet Doe may be John Doe's mother. John Doe may have access to the health feeds for the members of his family (Amy and Harriet), whose health care he manages to some extent. The exemplary graphical user interface allows a user to tab between various patients 702-704, which varies the highlighted feed in the user interface 700, 709, 719. In FIG. 7A, a graphical user interface 700 may include identification information 701. Graphical user interface 700 displays the health feed displays 705-708 for John Doe 702. However, if John Doe wishes to view the health feed information for his daughter; he may select the "Amy Doe" tab 703. Alternately, John Doe may select the "Harriet Doe" tab 704 to view health feed information for his mother. The tabs illustrated in the figures are merely exemplary and the patient displays may be rendered in any appropriate organizational format.

In FIG. 7B, with the "Amy Doe" tab 712 selected, a graphical user interface 709 may display identification information 710 and the health feed information 714-717 for Amy Doe. Thus, John Doe may view and manage the health care recommendations and assessments for his dependents. John Doe may input information to be communicated with Amy Doe's providers and/or view assignments from Amy Doe's providers. Similarly, with the "Harriet Doe" tab selected 722 in FIG. 7C, the graphic user interface 719 may display identification information 718 and the health feed information 723-726 for Harriet Doe. John Doe may also view and manage the health care recommendations and assessments for his mother. While in the exemplary graphical user interface, three patients 720-722 are displayed, more patients may be added as the user group or family grows. Patients may also be removed; for example, as Amy Doe grows up and wishes to manage her own health care assessments and recommendations. Health feed displays and assessments displayed in the multi-patient graphical user interface may include any combination or permutation of the previously discussed examples.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and may be used in a selected embodiment, even if not specifically shown or described.

What is claimed is:

1. A computerized method carried out by a server having at least one processor for providing health care assessments for a patient and one or more family members of the patient, the method comprising:
   receiving provider inputs regarding the patient or the one or more family members of the patient;
   storing the provider inputs;
   determining, using the at least one processor, based on patient rules, provider information from the provider inputs to display to the patient or the one or more family members of the patient, the provider information comprising one or more of tests performed, treatments administered, clinician notes, and clinician recommendations;
   determining at least one patient input field to display;
   displaying the at least one patient input field;
   receiving inputs from the patient or the one or more family members of the patient, using the at least one patient input field, the inputs comprising one or more of weigh-in information, blood sugar monitoring information, personal physical assessments, and food diary entries;
   storing the inputs in the patient or the one or more family members of the patient records;
   determining at least one assessment for the patient or the one or more family members of the patient based on the inputs, the patient or the one or more family members of the patient records, and one or more user-generated rules; and
   simultaneously displaying on a single user interface a plurality of selectable options, at least a first selectable option of the plurality of selectable options corresponding to the patient and at least a second selectable option of the plurality of selectable options corresponding to the one or more family members of the patient, wherein selection of at least one of the plurality of selectable options initiates the simultaneous display of the provider information from the provider inputs and the at least one assessment.

2. The method of claim 1, wherein the at least one patient input field comprises a patient questionnaire.

3. The media of claim 2, wherein the least one assessment for the patient comprises a questionnaire results summary.

4. The method of claim 1, wherein determining the at least one patient input field to display to the patient is determined by patient type.

5. The method of claim 1, wherein the provider inputs comprise medical test results from clinical testing.

6. One or more non-transitory computer-storage media having computer-executable instructions embodied thereon that, when executed by a computing device, cause the computing device to generate a graphical user interface that simultaneously displays a plurality of selectable options corresponding to at least a patient and one or more family members of the patient and the simultaneous display of multiple health feeds upon selection of one of the plurality of selectable options, the graphical user interface comprising:
   a display area configured to simultaneously present at least a first selectable option of the plurality of selectable options corresponding to the patient and at least a second selectable option of the plurality of selectable options corresponding to the one or more family members of the patient, wherein selection of at least one of the plurality of selectable options initiates the simultaneous display of a first, second, and third health feed, wherein:
   the first health feed comprises clinical information for the patient or the one or more family members of the patient comprising one or more of tests performed, treatments administered, clinician notes, and clinician recommendations;
   the second health feed comprises patient-generated information for the patient or the one or more family members of the patient comprising one or more of weigh-in information, blood sugar monitoring information, personal physical assessments, and food diary entries; and the third health feed comprises feedback information comprising patient feedback on the clinical information for the patient or the one or more family members of the patient and the patient-generated information for the patient or the one or more family members of the patient.

7. The graphical user interface of claim 6, wherein the feedback information further comprises clinical feedback on the patient-generated information of the second health feed display.

8. The graphical user interface of claim 6, wherein the feedback information further comprises one or more patient questionnaires.

9. The graphical user interface of claim 8, wherein the feedback information further comprises a summary of patient questionnaire results.

10. The graphical user interface of claim 6, wherein the feedback information further comprises request displays for requests for patient activity, requests for clinic activity, or a combination thereof.

11. One or more non-transitory computer-storage media having computer-executable instructions embodied thereon that, when executed by a computing device, cause the computing device to generate a graphical user interface that simultaneously displays a plurality of selectable options corresponding to at least a patient and one or more family members of the patient and the simultaneous display of multiple health feeds upon selection of one of the plurality of selectable options, the graphical user interface comprising:

a display area configured to simultaneously present at least a first selectable option of the plurality of selectable options corresponding to the patient and at least a second selectable option of the plurality of selectable options corresponding to the one or more family members of the patient, wherein selection of at least one of the plurality of selectable options initiates the simultaneous display of a first, second, and third health feed, wherein:

the first health feed comprises clinical information for the patient or the one or more family members of the patient comprising one or more of tests performed, treatments administered, clinician notes, and clinician recommendations;

the second health feed comprises patient-generated information for the patient or the one or more family members of the patient comprising one or more of weigh-in information, blood sugar monitoring information, personal physical assessments, and food diary entries; and the third health feed comprises feedback information comprising clinical feedback on the patient-generated information for the patient or the one or more family members of the patient of the second health feed display.

12. The graphical user interface of claim 11, wherein the feedback information further comprises patient feedback on at least one of the clinical feedback and the clinical information of the first health feed display.

13. The graphical user interface of claim 11, wherein the feedback information further comprises one or more patient questionnaires.

14. The graphical user interface of claim 13, wherein the feedback information further comprises a summary of patient questionnaire results.

15. The graphical user interface of claim 11, wherein the feedback information further comprises request displays for requests for patient activity, requests for clinic activity, or a combination thereof.

* * * * *